United States Patent [19]

Bowden

[11] Patent Number: 4,699,611

[45] Date of Patent: Oct. 13, 1987

[54] BILIARY STENT INTRODUCER

[75] Inventor: Russell W. Bowden, Tyngsboro, Mass.

[73] Assignee: C. R. Bard, Inc., Murray Hill, N.J.

[21] Appl. No.: 725,137

[22] Filed: Apr. 19, 1985

[51] Int. Cl.⁴ ............................................ A61M 25/00
[52] U.S. Cl. ...................................... 604/51; 604/105; 604/165; 128/343
[58] Field of Search ............. 604/53, 93, 51, 104–106, 604/164–166, 281; 128/325, 329, 341–345, 330

[56] References Cited

U.S. PATENT DOCUMENTS

| | | | |
|---|---|---|---|
| 2,770,236 | 11/1956 | Utley et al. | 604/166 |
| 3,344,791 | 10/1967 | Foderick | 604/104 |
| 3,530,860 | 9/1970 | Majoros | 604/264 X |
| 3,565,074 | 2/1971 | Foti | 604/164 |
| 3,788,318 | 1/1974 | Kim et al. | 604/104 |
| 3,807,408 | 4/1974 | Summers | 604/104 |
| 4,411,655 | 10/1983 | Schreck | 604/165 |
| 4,451,256 | 5/1984 | Weikl et al. | 604/164 |
| 4,502,482 | 3/1985 | DeLuccia et al. | 604/165 |

*Primary Examiner*—Dalton L. Truluck
*Attorney, Agent, or Firm*—Wolf, Greenfield & Sacks

[57] ABSTRACT

A device and technique for percutaneous placement of a tubular prosthesis involves gripping the leading end of the prosthesis by an expandable member inserted into the lumen of the prosthesis from the trailing end of the prosthesis. The expandable member grips the prosthesis at its leading end so that when the member is pushed to advance it into and through the patient, it will tension the prosthesis. The prosthesis has radially extending portions which will serve to retain the prosthesis in place once implanted. During insertion, the tensioning of the prosthesis causes the radial projections to be drawn into a collapsed configuration to define a substantially continuous tubular shape along the full length of the prosthesis.

20 Claims, 23 Drawing Figures

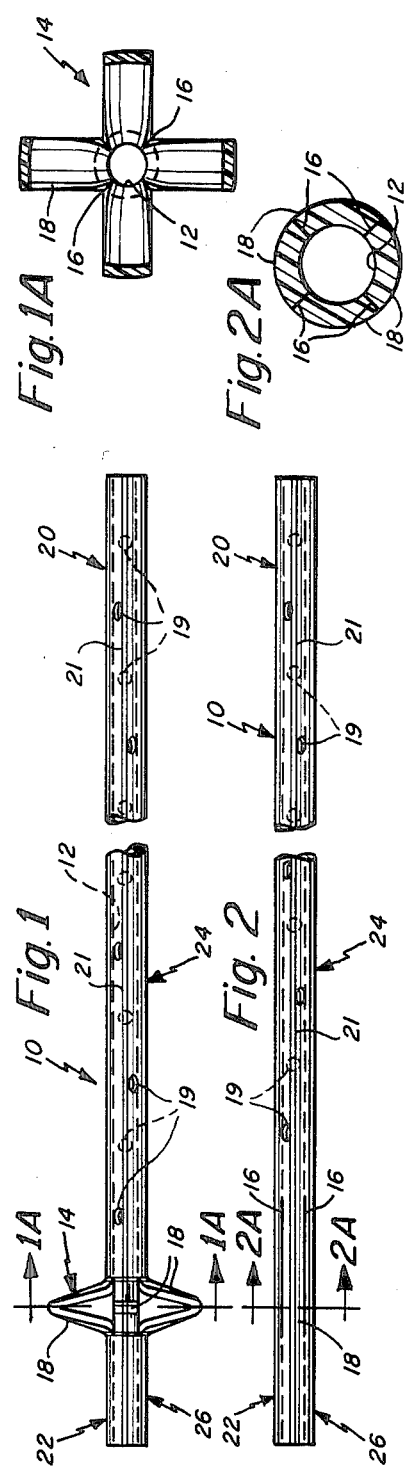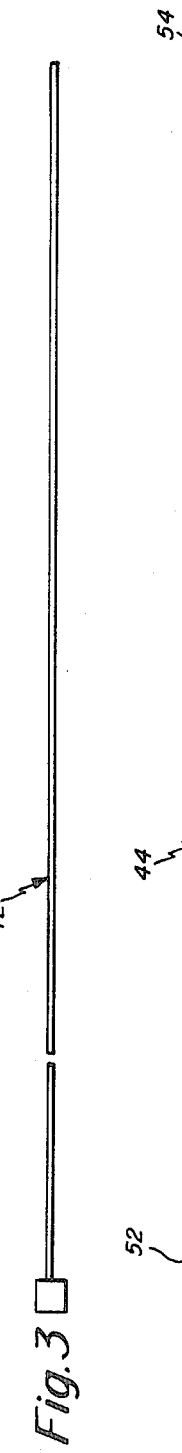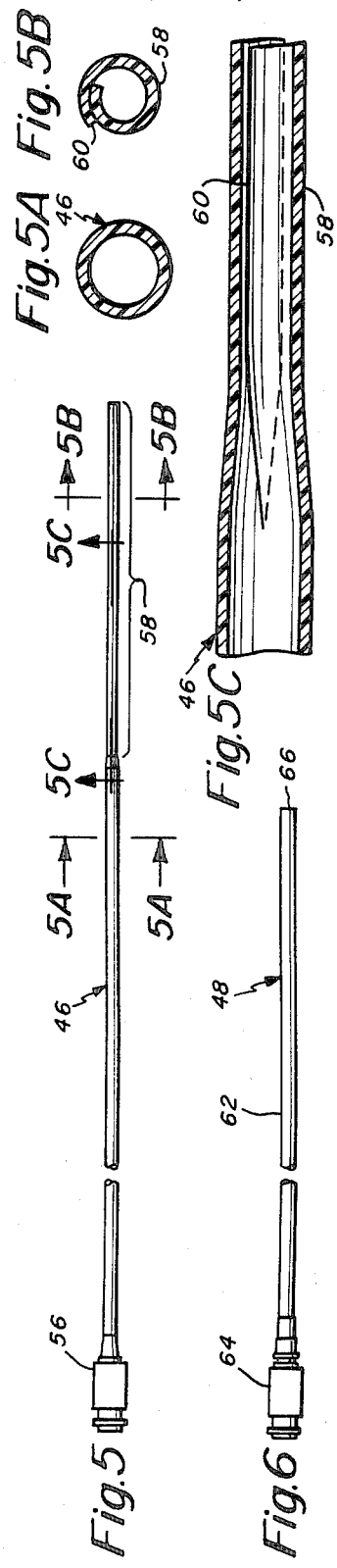

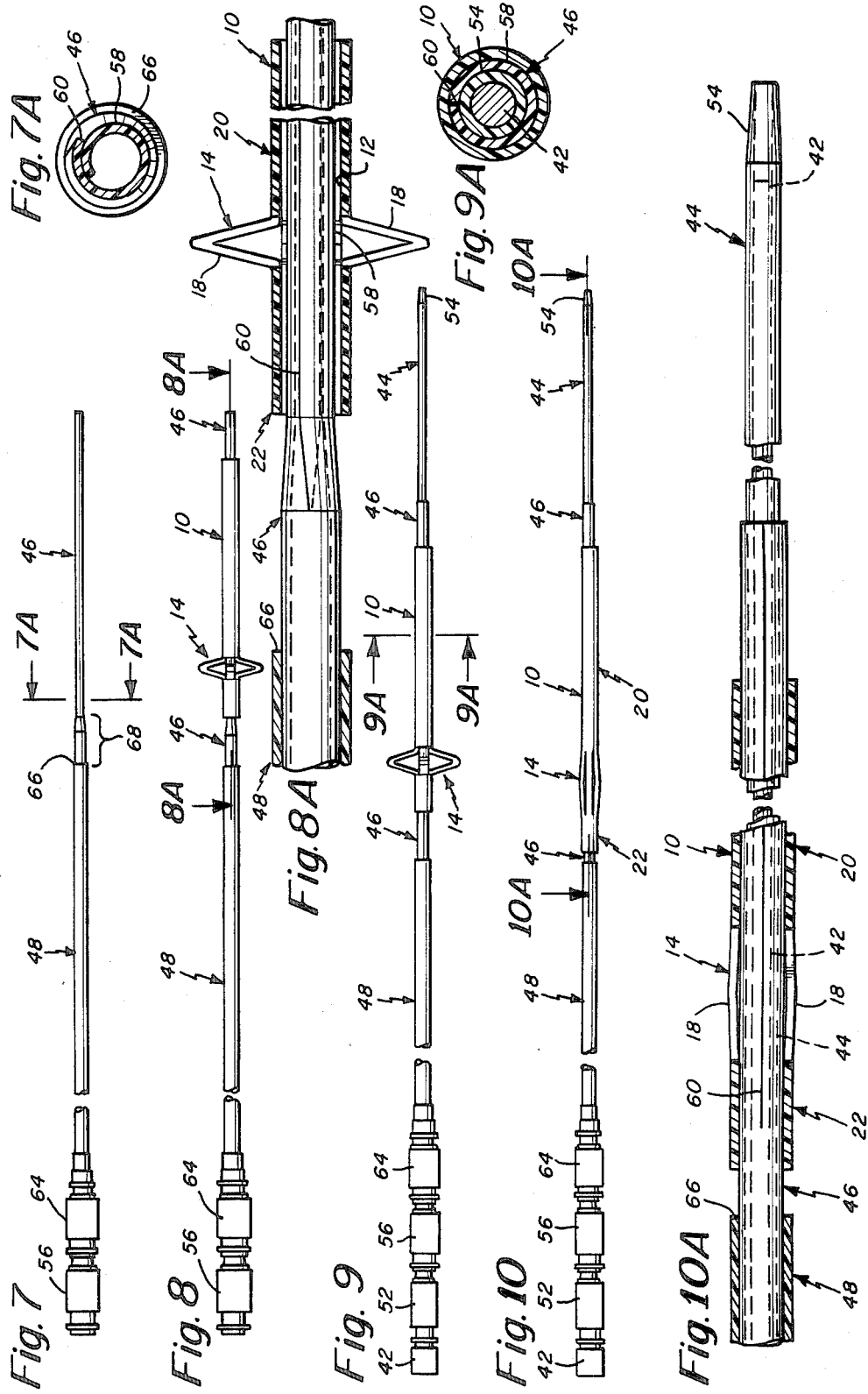

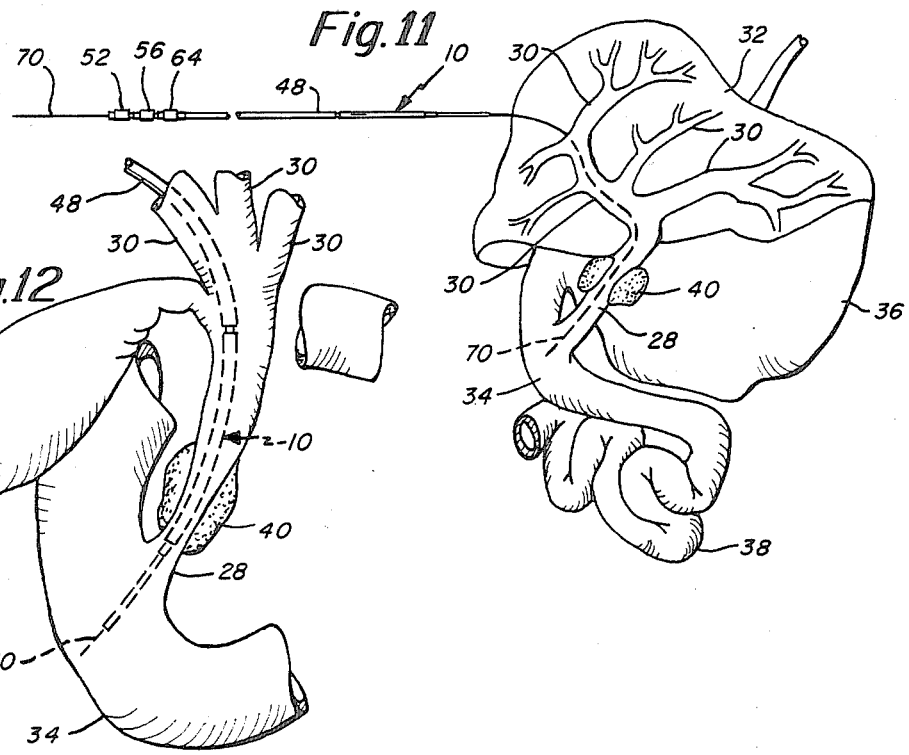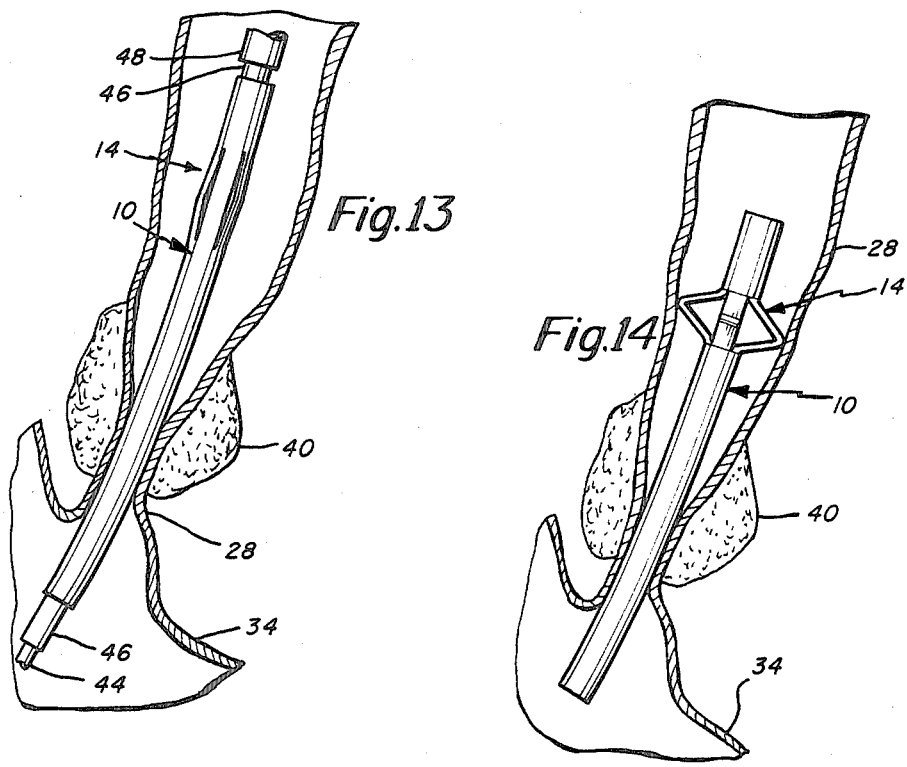

BILIARY STENT INTRODUCER

FIELD OF THE INVENTION

This invention relates to devices and techniques for percutaneous placement of a tubular prosthesis within a duct or vessel of a patient, such as the biliary duct.

BACKGROUND OF THE INVENTION

The placement of tubular prosthesis in various vessels is desirable in the treatment of a number of medical conditions. For example, where a vessel or a passage is obstructed it may be desirable to insert a prosthetic tube within the vessel to maintain the passage in an open condition. Such a technique may be indicated in various conditions such as where the vessel is constricted by a tumor in a manner which tends to restrict or block the flow of fluid through the vessel thus disrupting proper functioning of the vessel. One such condition is constriction or stenosis of the bile duct which may result from a tumor surrounding the duct. It is difficult to correct such a condition surgically and often the condition may not be correctable by resection. Because constriction of the bile duct causes various difficulties such as jaundice and numerous other difficulties. An external drain provides a continuous risk for infection because it presents a path for bacteria to enter the body. Additionally, there is always the risk that the tube may be inadvertently pulled out. Moreover, external drainage prevents essential bile salts from entering the digestive tract. In order to replace the bile salts it is a common procedure to have the patient drink the bile liquid collected through the drainage tube. It is essential that the condition be alleviated promptly. Often this is achieved by inserting a drainage tube percutaneously and into the bile tree of the patient's liver to permit bile to drain.

Another technique is to insert a prostethic tube into the bile duct to maintain the flow passage open through the bile duct. This technique often is preferred because it avoids complicated surgery and can be completed in a relatively short period of time. It is preferred to the drainage tube approach because continued use of a drainage tube increases the risk of infection. Prosthetic tubes may be placed in the bile duct by a number of techniques which involve insertion of catheters, probes and various devices to guide, manipulate and position the prosthesis.

One such technique is described by G. Mendez, Jr., et al percutaneous brush biopsy and internal drainage of biliary tree through endoprosthesis American Roentgen Ray Society April 1980, Pages 653-659. Mendez describes the percutaneous transhepatic placement of a tubular prosthesis which is flared at its proximal end and tapered at its distal end. The procedure involves insertion of a needle through the patient's skin and through the patient's liver to puncture a branch of the biliary tree. A guide wire then is inserted through the needle and is advanced into and through the biliary tree. The needle is removed and a catheter then is passed over and along the guide wire to place the catheter within the patient with its distal end extending into the bile duct. The prosthesis, which fits slidably over the placed catheter then is advanced over the catheter and a pusher tube, which also fits slidably over the guiding catheter, is used to push the prosthesis through the patient along the catheter to a position within the bile duct. After the prosthesis has been placed the catheter, pusher tube and guide wire may be removed.

The procedure is traumatic to the liver and can be quite painful for the patient, particularly because of the enlarged diameter at the flared proximal end of the prosthesis. The flared proximal end, however, is essential if the prosthesis is to remain properly in place within the bile duct. In the absence of an enlargement on the prosthesis, such as the flared proximal end, natural peristaltic action would tend to advance the prosthesis out of the duct.

Another system is described by Kerlan et al, Biliary Endoprostheses, Radiology March 1984 pages 828-830. Kerlan describes the use of a technique in which a prosthetic tube is pushed from its trailing end while being pulled from its leading end. The technique uses a prosthetic tube having Mallecot tips formed at each of its ends. Mallecot tips are formed by a plurality of parallel longitudinal slits about the periphery of the tubular prosthetic to produce radially protruding lobes which can be heat set in a protruding or flowered position. Once the stent is positioned in the bile duct the flowered Mallecots prevent the peristaltic motion of the diatal bile duct from pulling the stent into the duodenum.

In the Kerlan procedure a guide wire is inserted percutaneously and transhepatically into and through the bile duct, duodenum, stomach, alimentary canal and out of the patient's mount. The stent is advanced into the patient by passing it over the guide wire at the mouth end and advancing it along the guide wire through alimentary canal, stomach, duodenum and into the bile duct. The stent is advanced by pulling it from its leading (hepatic) end while pushing it from its trailing (oral) end. In order to pull on the leading end of the stent a balloon catheter is passed over the guide wire from the percutaneously inserted end until the balloon tip is advanced to the patient's mouth. The balloon tip of the balloon catheter is inserted into the leading end of the stent and is positioned within the Mallecot tip. When the balloon is inflated it expands the Mallecot tip and becomes locked to it. The balloon catheter then may be withdrawn along the guide wire thereby pulling the stent by its leading end along the guide wire through the alimentary canal and toward the bile duct. Simultaneously a pusher tube is placed over the oral end of the guide wire and is used to push the stent from its trailing end. After the stent is positioned, the balloon catheter, pusher tube and guide wire are removed and the Mallecot's tips will remain in their expanded, flowered configuration to prevent migration of the stent from the biliary duct.

The technique described by Kerlan presents the same difficulty described above in connection with the Mendez technique in that the procedure results in an enlarged radial protrusion, in the form of the expanded Mallecot tip at each of the leading ends and trailing end. Thus, the technique described by Kerlan requires that the stent be forced through various passages while the Mallecot tips are in a flowered, enlarged configuration which makes it difficult and painful to advance and properly position the stent in the constricted bile duct.

The difficulties resulting from attempts to place a stent having flared or enlarged portion have been recognized. Koons et al, Large Bore, Long Biliary Endoprostheses (biliary stents) For Improved Drainage, Radiology July 1983 89-94 describes another technique in which the tubular stent does not have flared portions, Mallecot tips or other radial projections. Koons describes problems resulting from peristaltic migration of the stents and suggests that the problem might by overcome by using longer stents. However, even with a longer stent, there still remains a risk that the stent might be peristaltically advanced and discharged from the biliary duct.

It is among the general objects of the invention to provide an improved method and apparatus for placing a tubular stent which avoids the foregoing and other problems.

SUMMARY OF THE INVENTION

The present invention uses a technique in which the tubular stent is gripped at its leading end by an expandable member inserted into the lumen of the stent from the trailing end of the stent. The expandable member grips the stent at its leading end so that when the member is pushed to advance it into the patient it will tension the stent so that the lobes of a trailing Mallecot tip on the stent will be tensioned and will be drawn longitudinally into a radially collapsed configuration to define a substantially continuous tubular shape along the full length of the stent. The invention achieves this by gripping the stent in a manner in which the Mallecot tip trails the gripped portion of the stent.

A preferred stent which is used in the practice of the invention has a Mallecot tip formed at its trailing end. The leading end is tubular and has no Mallecot tip. Other stents having enlargements at the trailing end may be used such as, for example, a stent having a pigtail or curlicue at its trailing end.

The system for percutaneously and transhepatically placing the stent includes a carrier sheath, a pusher sheath which fits slidably over the carrier sheath and a dilator which fits slidably within the carrier sheath. The carrier sheath on which the stent is placed has a radially expandable distal portion which holds the stent securely during insertion. The distal portion of the carrier sheath is formed by slitting it longitudinally and curling the slit edges within one another. When so curled the distal portion of the carrier sheath defines a smaller outer diameter than the more proximal portion of the carrier sheath. The distal portion of the carrier sheath is insertable into the stent and is expandable so as to lock it to the stent by advancing a dilator into the carrier sheath to expand the distal portion.

The procedure involves first placing the pusher sheath coaxially over the carrier sheath so that the distal end of the carrier sheath protrudes beyond the pusher sheath. The protruding distal portion of the carrier sheath then is inserted into the stent through the proximal, trailing end of the stent. A stiffening stylet then is inserted into the dilator and the styleted dilator is inserted into the carrier sheath. As the dilator is pushed through the distal portion of the carrier sheath the distal portion expands to engage frictionally the lumen at the distal end of the stent and hold the stent securely. The proximal end of the stent then is tensioned and pulled proximally over on to the relatively large diameter proximal portion of the carrier sheath to collapse the Mallecot. The stylet then is removed and the system of the dilator, carrier sheath, pusher sheath and stent is threaded over a guide wire, which will have been percutaneously positioned through the bile duct and into the duodenum. Once the system has been advanced so that the stent is in its intended position in the bile duct the pusher sheath is advanced over the carrier sheath to push the trailing end of the stent onto the distal portion of the carrier sheath. That causes the Mallecot to flower at the trailing end of the bile duct. The dilator then is withdrawn from the carrier sheath to enable the distal end of the carrier sheath to radially contract and release its grip on the stent. Then the gripper sheath and pusher sheath can be removed. The flowered Mallecot will serve to maintain the stent in position and to prevent peristaltic migration of the stent.

The stent thus is advanced through and positioned in the patient while maintaining the stent in a substantially tubular configuration with the Mallecot tip collapsed. The difficulties previously encountered in connection with percutaneous transhepatic placement of biliary stents are avoided.

It is among the general objects of the invention to provide an improved method and apparatus for percutaneously advancing a tubular prosthetic member to a selected location within a patient.

Another object of the invention is provide an improved method and apparatus for placing a prosthetic tube having a Mallecot tip in which the Mallecot tip is maintained in a collapsed configuration during insertion.

A further object of the invention is to provide an improved method and apparatus for percutaneously and transhepatically placing a biliary stent.

DESCRIPTION OF THE DRAWINGS

The foregoing and other objects and advantages of the invention will be appreciated more fully from the following further description thereof, with reference to the accompanying drawings wherein:

FIG. 1 is a side view of a biliary stent having a Mallecot tip showing the tip in its relaxed flowered condition;

FIG. 1A is a sectional illustration of the stent as seen along the line 1A—1A of FIG. 1;

FIG. 2 is an illustration of the stent with the Mallecot tip collapsed radially.

FIG. 2A is cross sectional illustration of the collapsed Mallecot tip as seen along the line 2A—2A of FIG. 2;

FIGS. 3-6 illustrate the elements of the stent introducer and placement system including, respectively, the stiffening stylet, the dilator, the carrier sheath and the pusher sheath, arranged to illustrate their relative lengths;

FIGS. 5A, 5B and 5C are sectional illustrations of the carrier sheath as seen along the lines 5A—5A, 5B—5B and 5C—5C, respectively, in FIGS. 5;

FIG. 7 is an illustration of the pusher sheath positioned on the carrier sheath with the assembly ready to receive stent;

FIG. 7A is a cross sectional illustration as seen along the line 7A—7A of FIG. 7;

FIG. 8 is an illustration of the stent mounted on the combined pusher and carrier sheaths;

FIG. 8A is a sectional illustration as seen along the line 8A—8A of FIG. 8;

FIG. 9 is an illustration of the combined dilator and stylet after insertion into the assembly as shown in FIG. 8;

FIG. 9A is a cross sectional illustration as seen along the line 9A—9A of FIG. 9;

FIG. 10 is an illustration of the assembly of FIG. 9 showing the stent mounted on the assembled introducer system with the Mallecot tip collapsed and in readiness to be introduced into the patient;

FIG. 10A is a sectional illustration along the line 10A—10A of FIG. 10;

FIG. 11 is an illustration of the liver and biliary system with a guide wire in place and showing the stent and introducer system partially advanced along the guide wire;

FIG. 12 illustrates the stent after the stent and system have been advanced to position the stent within the bile duct;

FIG. 13 is an enlarged illustration of FIG. 12 showing the stent in position prior to flowering of the Mallecot; and FIG. 14 is an illustration of the stent in place in the biliary duct with the Mallecot flowered and with the introducer set removed.

DESCRIPTION OF THE PREFERRED EMBODIMENTS

FIGS. 1 and 2 illustrate an embodiment of a stent, indicated generally by the reference character 10, which may be used in practicing the invention. The stent 10 is tubular and is formed from a flexible, biologically inert material such as thermoplastic elastomer. Stent 10 has a lumen 12 which extends fully through the length of the stent 10. The stent is provided with a Mallecot tip 14 which is defined by forming a plurality of longitudinal slits 16 (see FIG. 2) through the wall of the tubular stent 10. The slits 16 are circumferentially spaced about the stent. In the illustrative embodiment there are four such slits equally circumferentially spaced, which define four symmetrically arranged strips 18. The stent also may be made to have three strips. The Mallecot tip 14 may be "flowered" as illustrated in FIGS. 1 and 1A in which the strips 18 defined between the slits 16 bend to form radially protruding lobes circumferentially about the stent 10. When used as a biliary stent as described herein the stent is formed so that it will assume the flowered position when in a relaxed state. This may be achieved by heat setting the stent while in a flowered condition. The Mallecot may be collapsed radially inwardly as shown in FIG. 2 by longitudinally tensioning the stent 10.

The stent preferably is provided with a plurality of holes 19 extending longitudinally along and circumferentially about the stent to provide a substantial number of drainage holes.

The stent 10 preferably is formed to include at least one radiographic stripe 21 to enable the stent to be visualized fluoroscopically. The stripe may be formed by coextruding with the tube from which the stent is made, a strip of stent material filled with a radiopaque material such as barium sulfate. If desired, the stent may be formed in its entirety from thermoplastic elastomer filled with a radiopaque material such as barium sulfate.

In the illustrative embodiment, the stent may be considered as having a leading, distal end 20 and a proximal, trailing end 22. The Mallecot tip 14 is located near the proximal, trailing end 22 and may be considered as separating the stent into a distal segment 24 and a proximal segment 26.

The location and position in which the biliary stent is intended to be placed will be appreciated from FIGS. 11 and 14 which illustrate the biliary anatomy. As shown in FIG. 14 the stent 10 is intended to be located in the biliary duct 28 which connects the biliary tree 30 of the liver 32 to the duodenum 34 which connects the patient's stomach 36 to the small intestine 38.

FIG. 14 illustrates a condition which the stent 10 is intended to treat. As illustrated, the biliary duct 28 has become constricted as by a tumor 40 which has developed about the biliary duct 28 and which restricts or prevents drainage of bile into the duodenum 34 and into the patient's digestive tract. The constriction requires treatment either by inserting a drainage tube into the patient to permit the bile to drain externally of the patient or to place a tubular stent through the constricted portion of the biliary duct 28 to maintain a flow passage to the duodenum and the patient's digestive tract. The latter procedure is preferred because it permtis the patient to be mobile and, once placed, avoids the discomfort associated with external biliary drainage tubes. When the stent 10 is placed the Mallecot tip 14 will be in its flowered configuration to prevent the stent 10 from migrating downwardly through the biliary duct 28. The Mallecot tip 14, being located nearer to the trailing end 20 of the stent, serves to anchor the stent 10 in place. The flowered Mallecot tip cannot be advanced through the narrowed portion of the bile duct 28 by natural peristaltic action. The stent 10, so placed, maintains fluid flow communication from the bile tree 30 to the duodenum 34. Depending on the longitudinal location of the stent and the anatomy and condition of the patient, fluid from the bile tree can enter the stent through the opening at the trailing end of the stent or through the openings defined by the flowered Mallecot or through one or more of the holes formed longitudinally along the stent.

FIGS. 3–6 illustrate the elements of a set for introducing and placing the stent 10, percutaneously and transhepatically, in the biliary duct 28. The elements are arranged in the drawings to illustrate their respective lengths and include a stiffening stylet 42 (FIG. 3), a dilator 44 (FIG. 4), a carrier sheath 46 (FIG. 5) and a pusher sheath 48 (FIG. 6). Stiffening stylet 42 is solid wire and has an outer diameter such that it is slidably received within the lumen 50 of the dilator 44. Dilator 44 is a conventional commercially available dilator and is provided with a friction fitting 52 at its proximal end. The distal end of the dilator 44 is tapered as indicated at 54.

The dilator 44 may be formed from TFE or FEP plastic, such as Teflon.

The carrier sheath 46 is shorter than the dilator 44 and has a lumen 54 which is dimensioned to receive the dilator 44. The carrier sheath 46 also is provided with a friction fitting 56 at its proximal end to enable the fittings 52 and 56 to be frictionally connected when the dilator 44 is inserted fully into the carrier sheath 46.

The carrier sheath 46 also may be formed from a tube of TFE or FEP plastic. A distal segment 58 of the carrier sheath 46 is of smaller diameter than the more proximal portion of the carrier sheath 46. The reduced diameter distal segment 58 is radially expandable and is expanded by insertion of the dilator 44 through the carrier sheath 46. The reduced diameter radially expandable distal segment of the carrier sheath is formed by a longitudinally extending slit 60 and by curling the slit edges of the tubular wall of the distal segment 58 within one another as illustrated in FIG. 5B. As will be described in further detail, the inner diameter of the lumen 12 of stent 10 is greater than the reduced diameter of the distal segment 58 of the carrier sheath 46 to permit the collapsed distal segment 58 to pass freely through the lumen 12 of the stent 10. The diameter of the stent lumen 12, however, is slightly smaller than the outer diameter of the proximal portion of the carrier sheath 46. As will be described in further detail, the stent 10 can be securely attached to the carrier sheath by placing it over the distal segment 58 of the carrier sheath 46 and then inserting the dilator 44 into the carrier sheath 46 to expand radially the distal segment 58 into firm frictional engagement with the stent lumen 12.

The pusher sheath 48 is formed from a tube 62 of TFE or FEP plastic and has a friction fitting 64 secured to its proximal end. The diameter of the lumen of the pusher sheath 48 is such as to receive the larger diameter proximal portion of the carrier sheath 46. When the carrier sheath 46 is passed through the pusher sheath 48 they may be secured together by engagement of their frictional fittings 56, 64. The pusher sheath 48 is shorter than the carrier sheath 46 and has a distal end 66. When the carrier sheath 46 is advanced fully through the pusher sheath 48 the portion of the proximal segment of the carrier sheath 46 will protrude distally beyond the distal end 66 of the pusher sheath 48.

Preferably the materials from which the carrier sheath, pusher sheath and dilator are formed are filled with radiopaque material so that they can be fluoroscopically visualized.

By of illustrative example as to the dimensions of the elements of the system, the carrier sheath may be of the order of 52 centimeters long having an outer diameter of 7 French at its proximal portion. The dilator may be 57 centimeters long having a 7 French outer diameter. The stylet is between 56 to 57 centimeters long and it is made from stainless steel. The pusher sheath may be about 30 centimeters long with an inner diameter of the order of 8 to 9 French to accomodate the outer diameter of the 7 French carrier sheath. The stent may be of the order of 15 centimeters long having an outer diameter of about 12½ French and an inner diameter of approximately 0.100 inches.

FIGS. 7, 8 and 9 illustrate the sequence in which the components of the introducer system and the stent are assembled in preparation for placement in the patient. As shown in FIG. 7 the carrier sheath 46 is inserted through the pusher sheath 48 and the two are secured together by their frictional fittings 56, 64. A portion 68 of the proximal segment of the carrier sheath 46 protrudes distally beyond the distal end of the pusher sheath 48. As shown in FIG. 8 the stent 10 then is mounted on the distal segment of the carrier sheath 46 by advancing the combined pusher and carrier sheaths through the lumen 12 of the stent 10, with the Mallecot tip 14 located in a proximal position. The dilator 44 then is assembled with the stylet 42 by passing the stylet 52 through the dilator 44. The assembled stylet 42 and dilator 44 then are passed through the carrier sheath 50 with the friction fitting 52 of the dilator 44 being secured to the friction fitting 56 of the carrier sheath 46. As the dilator 44 advances through the distal segment 58 of the carrier sheath 46, the distal segment 58 is expanded radially outwardly against and into frictional engagement with the lumen 12 of the mounted stent 10. As shown in FIG. 9 the distal end of the dilator 44 protrudes distally beyond the distal end of the carrier sheath 46. The proximal end of the stent 10 then may be drawn proximally to draw it over the juncture point of the carrier sheath 46 and onto the larger diameter proximal position. That holds the stent 10 in its most elongated position and maintains the Mallecot 14 in a radially collapsed configuration so that the stent 10 defines a substantially smooth tubular configuration, as illustrated in FIG. 2. FIG. 9 illustrates the stent so positioned on the combined dilator, carrier sheath and pusher sheath. After the stent and components have been assembled as described, the stiffening stylet 42 is removed and the assembly is ready to be percutaneously and transhepatically introduced into the patient's biliary system.

FIG. 11 illustrates the manner in which the stent 10 is placed. A guide wire 70 will have been placed percutaneously previously in the patient. The guide wire extends into the biliary tree 30, downwardly through the biliary duct 28 and into the duodenum 34. The assembly of the dilator 44, sheaths 46, 48 and mounted stent are passed over the guide wire 70 and are advanced until the stent is located within the biliary tree and extends through the restricted portion. The positioning of the stent can be determined by reference to the radiopaque stripe on the stent 10. The stent is placed so that the Mallecot region will be disposed proximally of the stenosis. Once it has been determined that the stent is in the proper position, the dilator then is detached and is removed. Upon removal of the dilator the distal segment 58 of the carrier sheath contracts to release the distal portion of the stent 10. The friction fitting 56, 64 of the carrier and pusher sheaths 46, 48 then are released from each other and the pusher sheath 48 is advanced with respect to the carrier sheath 46 so that the distal end of the pusher sheath 66 engages the proximal end of the stent 10 and pushes the stent 10 off from engagement with the proximal segment of the carrier sheath while also assuring that the Mallecot tip 14 will flower into the configuration illustrated in FIG. 14. The carrier and pusher sheaths then may be withdrawn thus leaving the stent in place.

From the foregoing it will be appreciated that the invention permits percutaneous placement of a tubular member, such as a biliary stent which, when placed, is intended to have an enlarged projection such as a Mallecot tip. The invention enables percutaneous placement of such a device but without the difficulty and discomfort which would be encountered by advancing a device with a radial projection through relatively narrow passageways in the patient's body. The invention enables percutaneous placement of such a device while maintaining the radially projecting portion of the device in a collapsed configuration to facilitate advancement of the device through the patient's body and in a manner which, when the device is in place, enables the projection to expand.

It should be noted that although the invention is particularly useful in placement of a tubular member having a projection, such as a Mallecot tip, the invention also may be used in the percutaneous placement of other tubular members which do not have such radial projections. It should be understood, therefore, that the foregoing description of the invention is intended merely to be illustrative thereof and that other embodiments and modifications may be apparent to those skilled in the art without departing from its spirit.

Having thus described the invention what I desire to claim and secure by letters patent is:

1. An apparatus for percutaneous placement within a patient's body of an elongated tubular member having proximal and distal ends comprising:

an elongated tubular member;
an elongated flexible percutaneously insertable carrier member having a proximal end and a distal end, the distal end being constructed and arranged as to enable said tubular member to be detachably mounted on the distal end of said carrier member;

means for releasably locking the distal end of the carrier member to a distal portion of the tubular member without significantly enlarging the diameter of the tubular member, said releasable locking means comprising the distal portion of the carrier member being radially expandable and collapsible, whereby said tubular member and carrier member can be inserted percutaneously and may be advanced percutaneously in a distal direction by pulling the tubular member from its distal end in response to pushing on the proximal end of the carrier member.

2. An apparatus as defined in claim 1 wherein the carrier member comprises a tubular carrier sheath advanceable over a percutaneously placed guidewire.

3. An apparatus as defined in claim 1 further comprising pusher means supported on the carrier member for engaging the proximal end of the tubular member and for applying a distally directed pushing force to the proximal end of the tubular member.

4. An apparatus as defined in claim 3 wherein the pusher means comprises a pusher sheath slidable on the carrier sheath and being shorter than the carrier sheath, the distal end of the pusher sheath being engageable with the proximal end of the mounted tubular member.

5. An apparatus as defined in claim 4 wherein each of the carrier sheath and pusher sheath has a fitting at its proximal end, said fittings being detachably connectable to each other to enable the carrier sheath and pusher sheath to be detachably connected to each other.

6. An apparatus for percutaneous placement within a patient's body of an elongated tubular member having proximal and distal ends comprising:
an elongated flexible percutaneously insertable carrier member comprising a tubular carrier sheath advanceable over a percutaneously placed guidewire the carrier member having a proximal end and a distal end, the distal end being constructed and arranged as to enable said tubular member to be detachably mounted on the distal end of said carrier member;
said carrier member being insertable into the lumen of said tubular member;
means for releasably locking the distal end of the carrier member to a distal portion of the tubular member without significantly enlarging the diameter of the tubular member, said releasable locking means comprising the distal portion of the carrier member being radially expandable and collapsible, said radially expandable and collapsible distal portion of the carrier sheath comprising means forming a slit in the distal portion of the carrier sheath, the edges of the sheath which define said slit being curled so as to define a reduced diameter;
whereby said tubular member and carrier member can be inserted percutaneously and may be advanced percutaneously in a distal direction by pulling the tubular member from its distal end in response to pushing on the proximal end of the carrier member.

7. An apparatus as defined in claim 6 further comprising means for effecting said expansion and collapse of the distal portion of the carrier sheath.

8. An apparatus as defined in claim 7 wherein the means for effecting said expansion and collapse comprises a dilator insertable into and through the lumen of the carrier sheath, the dilator being dimension so as to expand the curled portions of the distal region of the carrier sheath to enlarge the diameter at the distal portion of the carrier sheath, said distal portion of the carrier sheath being constructed so that upon removal of the dilator, the sheath walls will return to their curled configuration.

9. An apparatus as defined in claim 8 further comprising a pusher sheath slidably mounted on the carrier sheath, the pusher sheath being shorter than the carrier sheath and having a distal end which is engageable with the proximal end of the mounted tube.

10. An apparatus as defined in claim 9 further comprising a fitting from the proximal end of each of the carrier sheath, dilator and pusher sheath, said fittings being constructed and arranged to enable the carrier sheath to be detachably connected to the pusher sheath and to enable the dilator to be detachably connected to the carrier sheath.

11. An apparatus as defined in claim 8 wherein said dilator comprises a tubular dilator sheath having an outer diameter receivable within the lumen of the carrier sheath, the distal portion of the dilator being tapered, the dilator being longer than the carrier sheath.

12. An apparatus as defined in claim 11 wherein the dilator is longer than the carrier sheath and the tubular member mounted thereto whereby the tapered distal end of the dilator will protrude distally beyond the carrier member and tube thereby to facilitate percutaneous entry and advancement of the combined carrier sheath, dilator and tubular member.

13. An apparatus as defined in claim 12 further comprising a stiffening stylet receivable within the lumen of the dilator to stiffen the dilator.

14. An apparatus as defined in claim 11 wherein each of the dilator and carrier sheath have a fitting at their proximal ends to enable said dilator and carrier sheath to be detachably secured together.

15. An apparatus for percutaneous placement within a patient's body of an elongated tubular member having proximal and distal ends comprising:
an elongated tubular member;
an elongated flexible percutaneously insertable carrier member having a proximal end and a distal end, the distal end being constructed and arranged as to enable said tubular member to be detachably mounted on the distal end of said carrier member:
said tubular member having a distal segment and a proximal segment, the tubular member having a radially extending projection between the distal and proximal segments; said radially extending projection being collapsible in response to a tension applied to the tubular member;
the distal portion of the carrier sheath being disposed within the distal portion of the tubular member and being locked thereto; and
means for applying a tension to the proximal end of the tubular member to collapse radially the radial projection whereby the tubular member may be mounted on the carrier member in said collapsed configuration.

16. An assembly as defined in claim 15 wherein the means for applying said tension to the tubular member comprises:
the proximal portion of the carrier member having a diameter which is frictionally receivable within the inner diameter of the lumen in the proximal segment of the tubular member, said proximal portion of said tubular member being drawn proximally over said proximal portion of the carrier member.

17. An assembly as defined in claim 16 further comprising:
a pusher member slidably mounted on the carrier member proximally of the tubular member, the pusher member having a distal end engageable with the proximal end of the tubular member, the pusher member being constructed and arranged so as to push the proximal segment of the tubular member off from engagement with the proximal portion of the carrier member.

18. A method for percutaneously placing an elongate tubular member comprising:
percutaneously placing a guidewire to provide a guiding means to the intended placement site of the tubular member;
mounting the tubular member on a carrier sheath in a manner in which the carrier sheath is detachably locked to a distal portion of the tubular member;
advancing the combined carrier sheath and tubular member over the guide wire and percutaneously to the intended placement site by pushing the proximal portion of the carrier member;
said tubular member being maintained in longitudinal tension throughout the advancement;
releasing the lock between the carrier member and tubular member when the tubular member has been advanced to its intended placement site; and
withdrawing the carrier member and guidewire thereby leaving the tubular member at its intended placement site.

19. A method of defined in claim 18 wherein the intended placement site for the tubular member comprises the biliary duct.

20. A method as defined in claim 19 wherein the tubular member has a Mallecot tip formed at its trailing end.

* * * * *